US00PP30319P3

(12) United States Plant Patent
Koot

(10) Patent No.: US PP30,319 P3
(45) Date of Patent: Mar. 26, 2019

(54) ***CALIBRACHOA* PLANT NAMED 'DUECALVOLPI'**

(50) Latin Name: ***Calibrachoa* sp.**
Varietal Denomination: Duecalvolpi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 20 days.

(21) Appl. No.: 15/530,753

(22) Filed: Feb. 22, 2017

(65) Prior Publication Data

US 2018/0242500 P1 Aug. 23, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC . A01H 5/02; A01H 5/025; A01H 5/12; A01H 5/00; A01H 6/82
See application file for complete search history.

(56) References Cited

U.S. PATENT DOCUMENTS

PP19,256 P2 * 9/2008 Pierce ..... A01H 5/02 Plt./413

OTHER PUBLICATIONS

Dummen Orange Volcano Pink Products 2018, retrieved on May 14, 2018, retrieved from the Internet at https://www.dummenorange.com/app/en/products/usa/calibrachoa/volcano-pink/PAT_43703, 4 pp. (Year: 2018).*

Galema's Greenhouse 2017 Spring Catalog, retrieved on May 14, 2018, retrieved from the Internet at http://www.galemas.com/GG2017CatalogWeb.pdf, cover p. 1, 3, 13, 52, 60, 75-76. (Year: 2017).*

* cited by examiner

*Primary Examiner* — June Hwu
(74) *Attorney, Agent, or Firm* — C. A. Whealy

(57) ABSTRACT

A new and distinct cultivar of *Calibrachoa* plant named 'Duecalvolpi', characterized by its compact, semi-upright to outwardly spreading, trailing and decumbent plant habit; freely branching habit; early and freely flowering habit; flowers with red purple and white bi-colored petals; and good garden performance.

1 Drawing Sheet

Botanical designation: *Calibrachoa* sp.
Cultivar denomination: 'DUECALVOLPI'.

BACKGROUND OF THE INVENTION

The present invention relates to a new and distinct cultivar of *Calibrachoa* plant, botanically known as *Calibrachoa* sp. and hereinafter referred to by the name 'Duecalvolpi'.

The new *Calibrachoa* plant is a product of a planned breeding program conducted by the Inventor in Rheinberg, Germany. The objective of the breeding program is to create new compact and early-flowering *Calibrachoa* plants with large, unique and attractive flowers.

The new *Calibrachoa* plant originated from a cross-pollination made by the Inventor in July, 2014 in Rheinberg, Germany of a proprietary selection of *Calibrachoa* sp. identified as code number AA13-004920-001, not patented, as the female, or seed, parent with a proprietary selection of *Calibrachoa* sp. identified as code number AA13-002649-006, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2016.

Asexual reproduction of the new *Calibrachoa* plant by vegetative terminal cuttings in a controlled greenhouse environment in Rheinberg, Germany since June, 2016 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duecalvolpi'. These characteristics in combination distinguish 'Duecalvolpi' as a new and distinct *Calibrachoa* plant:

1. Compact, semi-upright to outwardly spreading, trailing and decumbent plant habit.
2. Freely branching habit.
3. Early and freely flowering habit.
4. Flowers with red purple and white bi-colored petals.
5. Good garden performance.

The new *Calibrachoa* can be compared to plants of the female parent selection. Plants of the new *Calibrachoa* differ primarily from plants of the female parent selection in flower color as plants of the female parent selection have yellow-colored flowers.

The new *Calibrachoa* can be compared to plants of the male parent selection. Plants of the new *Calibrachoa* differ primarily from plants of the male parent selection in flower color as plants of the male parent selection have red-colored flowers. In addition, plants of the new *Calibrachoa* are more compact than plants of the male parent selection.

Plants of the new *Calibrachoa* can be compared to plants of *Calibrachoa* sp. 'Cal Paicoras', disclosed in U.S. Plant Pat. No. 19,256. In side-by-side comparisons, plants of the new *Calibrachoa* differ primarily from plants of 'Cal Paicoras' in the following characteristics:

1. Plants of the new *Calibrachoa* have larger leaves than plants of 'Cal Paicoras'.
2. Plants of the new *Calibrachoa* flower earlier than plants of 'Cal Paicoras'.
3. Plants of the new *Calibrachoa* are more freely flowering than plants of 'Cal Paicoras'.
4. Plants of the new *Calibrachoa* have larger flowers than plants of 'Cal Paicoras'.
5. Plants of the new *Calibrachoa* and 'Cal Paicoras' differ in flower color as plants of 'Cal Paicoras' have coral and light pink bi-colored flowers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph is a side perspective view of a typical flowering plant of 'Duecalvolpi' grown in a container.

DETAILED BOTANICAL DESCRIPTION

The aforementioned photograph and following observations, measurements and values describe plants grown during the summer in 22-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting and were 16 weeks old when the photograph and description were taken. In the following description, color references are made to The Royal Horticultural Society Colour Chart, 2001 Edition, except where general terms of ordinary dictionary significance are used.

Botanical classification: *Calibrachoa* sp. 'Duecalvolpi'.

Parentage:

*Female, or seed, parent*.—Proprietary selection of *Calibrachoa* sp. identified as code number AA13-004920-001, not patented.

*Male, or pollen, parent*.—Proprietary selection of *Calibrachoa* sp. identified as code number AA13-002649-006, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; medium density.

Plant description:

*Plant and growth habit*.—Compact, semi-upright to outwardly spreading to trailing and decumbent plant habit; freely branching habit with about eight primary lateral branches developing per plant; pinching enhances branching; dense and full appearance; vigorous growth habit; moderate growth rate.

*Plant height*.—About 19 cm.

*Plant diameter*.—About 64 cm.

Lateral branch description:

*Length*.—About 45 cm.

*Diameter*.—About 3 mm.

*Internode length*.—About 1.3 cm.

*Strength*.—Strong.

*Aspect*.—Initially upright to outwardly spreading to trailing and decumbent.

*Texture*.—Pubescent.

*Color*.—Close to 146C.

Leaf description:

*Arrangement*.—Before flowering, alternate, and after flowering, opposite; simple.

*Length*.—About 2.9 cm.

*Width*.—About 1 cm.

*Shape*.—Oblanceolate.

*Apex*.—Rounded.

*Base*.—Cuneate.

*Margin*.—Entire.

*Texture and luster, upper and lower surfaces*.—Pubescent; matte.

*Venation pattern*.—Pinnate; arcuate.

*Color*.—Developing leaves, upper surface: Close to 137B. Developing leaves, lower surface: Close to 137C. Fully expanded leaves, upper surface: Close to 137A; venation, close to 137A. Fully expanded leaves, lower surface: Close to 137C; venation, close to 137C.

*Petioles*.—Length: About 3.4 mm. Diameter: About 1.7 mm. Texture, upper and lower surfaces: Pubescent. Color, upper and lower surfaces: Close to 144A.

Flower description:

*Flower arrangement and habit*.—Single salverform flowers arising from leaf axils; freely flowering habit with usually about 370 to 400 flowers developing per plant during the flowering season; flowers face upright to outwardly.

*Fragrance*.—None detected.

*Natural flowering season*.—Early flowering habit, plants of the new *Calibrachoa* initiate and develop flowers about four to five weeks after planting; plants flower continuously from the spring throughout the summer in Germany.

*Flower longevity*.—Individual flowers last about seven to ten days on the plant; flowers not persistent.

*Flower diameter*.—About 2.2 cm.

*Flower length* (*height*).—About 2.1 cm.

*Flower throat diameter*.—About 6.8 mm.

*Flower tube length*.—About 1.4 cm.

*Flower tube diameter, base*.—About 1.8 mm.

*Flower buds*.—Length: About 2.4 cm. Diameter: About 3.3 mm. Shape: Elongated oblong. Texture: Pubescent. Color: Close to 2D.

*Corolla*.—Arrangement: Five petals fused at the base and opening into a flared trumpet; deeply lobed. Petal length from throat: About 1.2 cm. Petal lobe width: About 1.2 cm. Petal shape: Roughly spatulate. Petal apex: Rounded. Petal margin: Entire. Petal texture and luster, upper and lower surfaces: Smooth, glabrous; matte. Throat texture: Smooth, glabrous. Tube texture: Smooth, glabrous. Color: Petal, when opening, upper surface: Close to 66A; towards the margins, close to 69D. Petal, when opening, lower surface: Close to 62C. Petal, fully opened, upper surface: Close to 66A; towards the throat, tinged with close to 46B; towards the margins, close to 69D; venation, midvein conspicuous; close to 46B; color becoming closer to 80A with development. Petal, fully opened, lower surface: Close to 62D; venation, close to 36B. Throat: Close to 46B; proximally, close to 10A; venation, faintly conspicuous, close to 59A. Tube: Close to 154C; venation, close to 187A.

*Calyx*.—Arrangement: Star-shaped calyx with five sepals; sepals fused at the base. Sepal length: About 1.3 cm. Sepal width: About 2.3 mm. Sepal shape: Lanceolate. Sepal apex: Acute. Sepal margin: Entire. Sepal texture and luster, upper and lower surfaces: Pubescent; matte. Color, upper and lower surfaces: Close to 137A.

*Peduncles*.—Length: About 1 cm. Diameter: About 1 mm. Angle: About 45° from stem axis. Strength: Moderately strong. Texture: Pubescent. Color: Close to 144B.

*Reproductive organs*.—Stamens: Quantity: Six per flower. Filament length: About 8.2 mm. Filament color: Close to 154C. Anther shape: Ellipsoidal. Anther length: About 0.6 mm. Anther color: Close to 13B. Pollen amount: Scarce. Pollen color: Close to 13B. Pistils: Quantity: One per flower. Pistil length: About 8.8 mm. Style length: About 7.8 mm. Style color: Close to 145A. Stigma shape: Ellipsoidal. Stigma color: Close to 144A. Ovary color: Close to 145A. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 5° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Duecalvolpi' as illustrated and described.

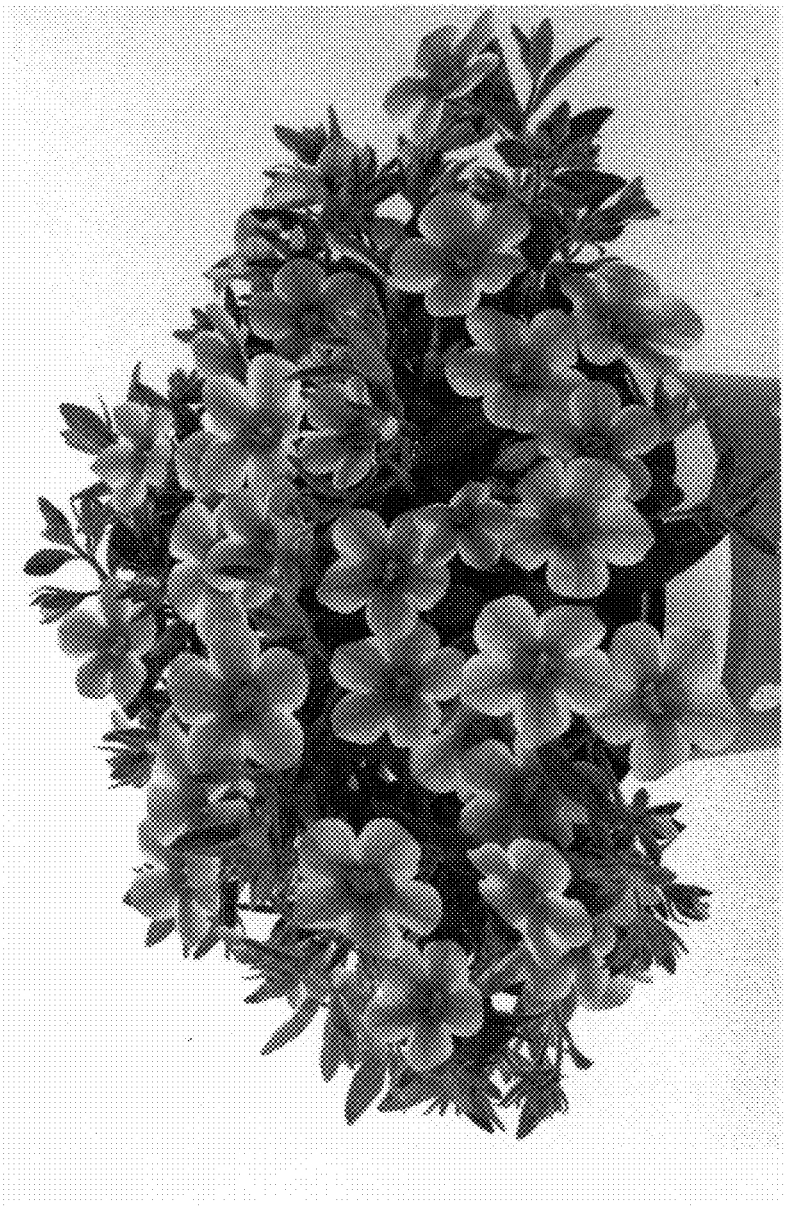

* * * * *